US00PP23779P3

(12) United States Plant Patent
Bradford

(10) Patent No.: US PP23,779 P3
(45) Date of Patent: Jul. 30, 2013

(54) INTERSPECIFIC TREE NAMED 'LATESWEET XXI'

(50) Latin Name: ***Prunus* sp.**
Varietal Denomination: LATESWEET XXI

(76) Inventor: Lowell Glen Bradford, Le Grand, CA (US)

( * ) Notice: Subject to any disclaimer, the term of this patent is extended or adjusted under 35 U.S.C. 154(b) by 81 days.

(21) Appl. No.: 13/374,026

(22) Filed: Dec. 8, 2011

(65) Prior Publication Data

US 2013/0152248 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford

*Primary Examiner* — Annette Para

(57) ABSTRACT

The present invention relates to an interspecific tree and more particularly to a new and distinct variety broadly characterized by a small size, moderately vigorous, hardy, and very productive tree. Being self-unfruitful, the present variety requires cross pollination from an apricot, interspecific, or plum that blooms during the mid to late season. The present variety produces a very heavy bloom with an abundant amount of pollen to entice good bee activity to facilitate pollination. The fruit matures under the ecological conditions described during the first week of November, with first picking on Nov. 2, 2011. The fruit is uniformly medium in size, very deep red in skin color, clingstone in type, globose to slightly oblong in shape, yellow in flesh color, firm in texture, and excellent in flavor.

1 Drawing Sheet

Botanical classification: *Prunus* sp.
Varietal denomination: 'LATESWEET XXI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'LATESWEET XXI'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2005 one such house containing a 'September Yummy®' plum tree (U.S. Plant Pat. No. 14,220) was crossed by me in this manner. To pollinate this plum tree, I selected bouquets from several sources of apricot and interspecific hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2008 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'September Yummy' (U.S. Plant Pat. No. 14,220) plum, by being self-unfruitful and by producing fruit that is juicy, firm in texture, full red to purple in skin color, and mostly yellow in flesh color, but is distinguished therefrom by producing fruit that is smaller in size, much sweeter in flavor, and that matures about fifty days later.

SUMMARY OF VARIETY

The present interspecific variety is characterized by a small size, moderately vigorous, hardy, and very productive tree. Being self-unfruitful, the present variety requires cross pollination from an apricot, interspecific, or plum that blooms during the mid to late season. The present variety produces a very heavy bloom with an abundant amount of pollen to entice good bee activity to facilitate pollination. The fruit matures under the ecological conditions described during the first week of November, with first picking on Nov. 2, 2011. The fruit is uniformly medium in size, very deep red in skin color, clingstone in type, globose to slightly oblong in shape, yellow in flesh color, firm in texture, and excellent in flavor.

DRAWING

The accompanying photograph consists of four whole fruits positioned to display the characteristics of the skin color and form, two half fruits divided to reveal the flesh and stone, one cleaned stone, typical leaves, and one inset depicting the blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the picking ripe, Nov. 2, 2011, on the original tree during its sixth growing season. The flower and bud descriptions were developed during the previous blooming season. All major color code designations are by reference to the Inter-Society Color Council, National Bureau of Standards. Common color names are also used occasionally.

PARENTAGE

Seed parent: 'September Yummy®' (U.S. Plant Pat. No. 14,220).

Pollen parent: Unknown.

TREE

Size: Small, reaching and maintaining a height of 10' [3.05 m.] and a spread of 5' [1.52 m.] after six growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a Perpendicular "V".

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming apricot, interspecific or plum such as 'Plumsweet IX' interspecific tree (U.S. Plant Pat. No. 18,666).

Bearing: Regular bearing observed thus far, weather dependent.

Trunk:

*Size.*—Medium, reaching a maximum diameter of 3¼" [82.6 mm.] after the sixth growing season.

*Texture.*—Shaggy.

*Bark color.*—A Strong brown [55. s.Br] and Dark brown [59. d.Br] variegation with Light yellowish brown [76. l.yBr] crevices present.

*Lenticels.*—Approximate Number Per Square Inch: 4. Color: Light yellowish brown [76. l.yBr]. Average Size: ¼" [6.4 mm.]. Shape: Eye-shaped, elongated.

Branches:

*Size.*—Diameter of Main scaffold is 1¼" [31.8 mm.] measured 12" above the first crotch, diameter of limb is ¾" [19.1 mm.] measured 12" above first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Dark yellowish brown [78. d.yBr] and Grayish brown [61. gy.Br] variegation.

*Lenticels.*—Number Per Square Inch: About 80 on second year wood. Color: Light yellowish brown [76. l.yBr]. Size: 1/64" [0.4 mm.] to 1/16" [1.6 mm.]. Shape: Eye-shaped, elongated.

Leaves:

*Size.*—Medium. Average Length: 3 5/16" [84.2 mm.]. Average Width: 1⅜" [34.9 mm.].

*Arrangement.*—Alternate.

*Thickness.*—Medium.

*Form.*—Elliptical.

*Apex.*—Acuminate.

*Base.*—Acute with an average angle base angle of 70 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Strong yellow green [117. s.YG] with some Grayish red [19. gy.R] areas where exposed to direct sunlight.

*Stipules.*—Number: Usually 2 per leaf, up to 6 per growing tip. Average Length: ¼" [6.4 mm.]. Color: Moderate yellowish brown [77. m.yBr].

*Glands.*—Number: 1 to 4 per leaf, mostly 2. Position: Mostly alternate, positioned at the intersection of the petiole and the leaf blade. Size: Medium. Form: Globose. Color: Light yellow green [119. l.YG] becoming Dark yellowish brown [78. d.yBr] in the center with age. Leaf buds. — Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1 1/16" [27.0 mm.].

*Number of petals.*—Five, no double blossoms observed.

*Petal shape.*—Oval to circular.

*Petal margin.*—Entire, quite wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Moderate orange [53. m.O] over a Brilliant yellow [83. brill.Y] center.

*Stigma color.*—Pale yellow [89. p.Y].

*Sepal color.*—Light yellow green [119. l.YG] on the outer surface with Grayish pink [8. gy.Pk] toward the edges on some.

*Sepal length.*—3/16" [4.8 mm.].

*Sepal width.*—5/32" [4.0 mm.].
*Sepal apex.*—Rounded to elliptical to match the width and length.
*Sepal margin.*—Fairly smooth with slight serrations toward the apex.
*Average pistil length.*—11/16" [17.5 mm.].
*Average stamen length.*—½" [12.7 mm.].
*Fragrance.*—Moderate.
*Bloom density.*—Very heavy.
*Number per cluster.*—2 to 10, average 5.
*Pollen production.*—Strong, good enticement to bees.
*Blooming period.*—Mid to late, with 'Santa Rosa' plum (unpatented).
*Onset of bloom.*—One percent on Mar. 4, 2011.
*Date of full bloom.*—Mar. 11, 2011.
*Duration of bloom.*—One to two weeks, dependent on ambient temperature.

FRUIT

Maturity when described: Picking ripe, Nov. 2, 2011.
Date of first picking: Nov. 2, 2011.
Date of last picking: Nov. 16, 2011.
Size: Uniform, small to medium.
*Average diameter axially.*—2⅜" [60.3 mm.].
*Average diameter across cheek plane.*—2 5/16" [58.7 mm.].
*Average diameter across suture plane.*—2 5/16" [58.7 mm.].
*Typical weight.*—4.0 ounces [113 grams].
Form: Uniform, globose to slightly oblong, symmetrical.
*Longitudinal section form.*—Round to slightly oblong.
*Transverse section through axial diameter.*—Round.
Suture: An inconspicuous line located in a shallow groove extending from the base to the apex.
Ventral surface: Slightly rounded, lipped toward the base on both sides.
Lips: Slightly unequal.
Cavity: Flaring, elongated in the suture plane, suture showing on one side.
*Depth.*—5/16" [7.9 mm.].
*Breadth.*—⅝" [15.9 mm.].
Base: Slightly truncate, somewhat cordate if viewed parallel to the suture.
Apex: Rounded, some with a slight hump.
Pistil point: An inconspicuous Pale orange yellow [73. p.OY] dot located at the end of the suture.
Stem: Medium.
*Average length.*—7/16" [11.1 mm.].
*Average width.*—⅛" [3.2 mm.].
Skin:
*Thickness.*—Medium.
*Surface.*—Smooth.
*Tenacity.*—Tenacious to the flesh.
*Astringency.*—Nonastringent.
*Tendency to crack.*—None observed in dry season.
*Color.*—Very deep red [14. v.deep R] over a Deep red [13. deep R] background with a moderate amount of Light orange yellow [70. l.OY] freckling throughout.
*Bloom.*—Abundant.
Flesh:
*Color.*—Brilliant greenish yellow [98. brill.gY].
*Surface of pit cavity.*—Covered with Dark yellow [88. d.Y] broken fibers when twisted away from stone.
*Amygdalin.*—Scarce.
*Juice.*—Moderate, rich.
*Texture.*—Firm, crisp, meaty.
*Fibers.*—Few, fine, tender.
*Ripens.*—Slightly earlier toward the apex.
*Flavor.*—Sweet with slight acid, typically 24 brix.
*Aroma.*—Very slight.
*Eating quality.*—Excellent.

STONE

Type: Clingstone.
Form: Oval.
Hilum: Narrow.
Base: Slightly cordate.
Apex: Acute with a very sharp 1/16" [1.6 mm.] tip.
Sides: Equal.
Surface: Rough throughout with a vertical ridge on each side of the dorsal fin.
External color of stone: Light olive brown [94. l.OlBr] when dry.
Pit wall color when cracked: Deep yellow [85. deep Y].
Cavity surface color: Pale greenish yellow [104. p.gY].
Average pit wall thickness: ⅛" [3.2 mm.]
Average width: ⅝" [15.9 mm.].
Average length: 1" [25.4 mm.].
Average breadth: ⅜" [9.5 mm.].
Tendency to split: None observed.
Kernel:
*Form.*—Oval.
*Skin color.*—Light olive brown [94. l.OlBr].
*Pellicle color.*—Moderate olive brown [95. m.OlBr].
*Vein color.*—Moderate olive brown [95. m.OlBr].
*Taste.*—Bitter.
*Viable.*—Yes.
*Average width.*—¼" [6.4 mm.].
*Average length.*—½" [12.7 mm.].
*Amygdalin.*—Scant.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'September Yummy' (U.S. Plant Pat. No. 14,220) plum, by being self-unfruitful and by producing fruit that is juicy, firm in texture, full red to purple in skin color, and mostly yellow in flesh color, but is distinguished therefrom by producing fruit that is smaller in size, much sweeter in flavor, and that matures about fifty days later.

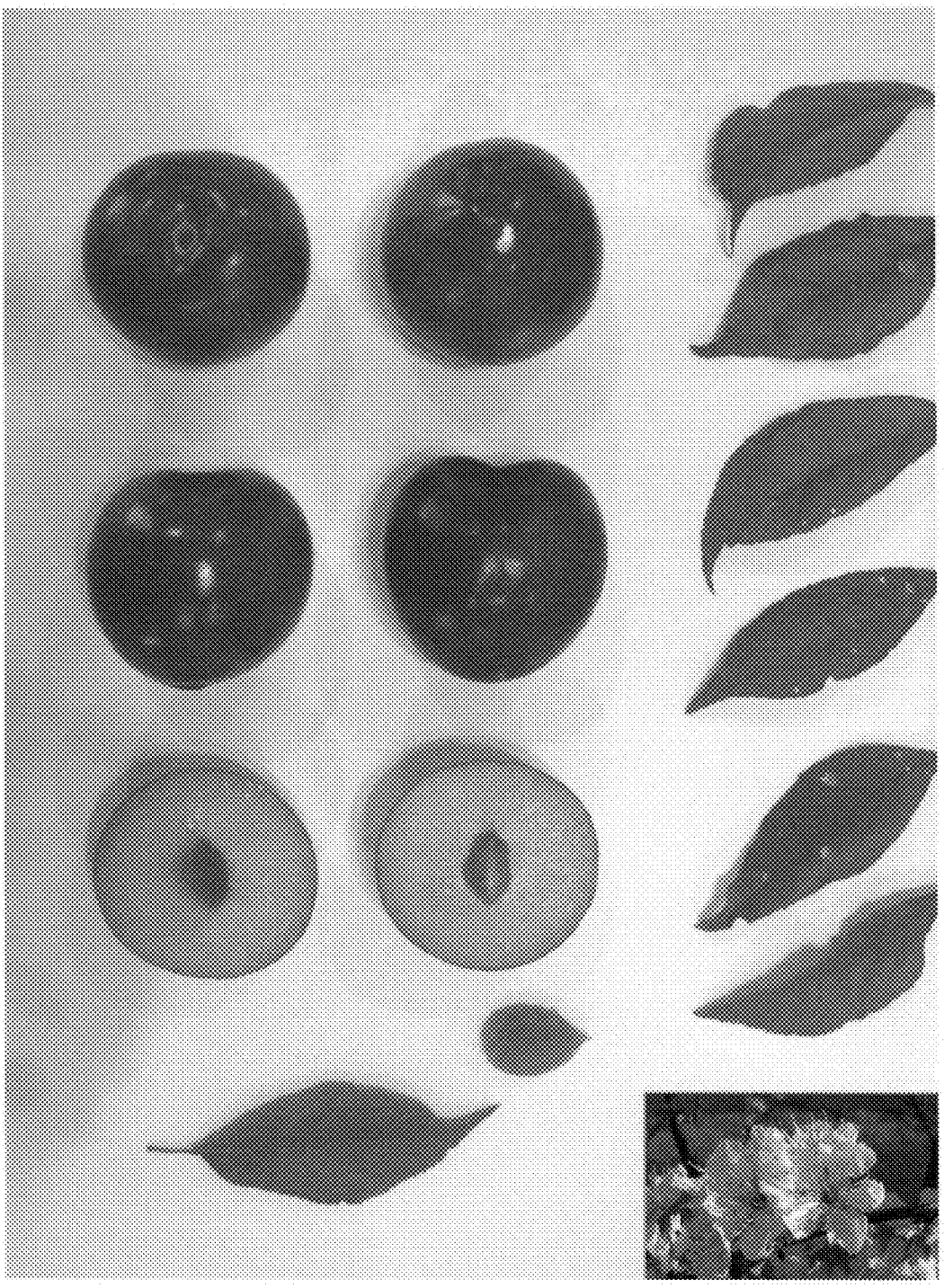

* * * * *